US009448203B2

United States Patent
Easton et al.

(10) Patent No.: US 9,448,203 B2
(45) Date of Patent: Sep. 20, 2016

(54) CLEANING OF CORONA DISCHARGE ION SOURCE

(71) Applicants: Matt Easton, Watford (GB); Stephen Taylor, Watford (GB); Bruce Grant, Watford (GB); Henry McIntyre, Watford (GB); Alastair Clark, Watford (GB)

(72) Inventors: Matt Easton, Watford (GB); Stephen Taylor, Watford (GB); Bruce Grant, Watford (GB); Henry McIntyre, Watford (GB); Alastair Clark, Watford (GB)

(73) Assignee: Smiths Detection—Watford Ltd. (GB)

( * ) Notice: Subject to any disclaimer, the term of this patent is extended or adjusted under 35 U.S.C. 154(b) by 0 days.

(21) Appl. No.: 14/430,181

(22) PCT Filed: Sep. 20, 2013

(86) PCT No.: PCT/GB2013/052469
§ 371 (c)(1),
(2) Date: Apr. 30, 2015

(87) PCT Pub. No.: WO2014/045051
PCT Pub. Date: Mar. 27, 2014

(65) Prior Publication Data
US 2015/0226704 A1    Aug. 13, 2015

Related U.S. Application Data

(60) Provisional application No. 61/704,031, filed on Sep. 21, 2012.

(51) Int. Cl.
*H01J 49/16*    (2006.01)
*G01N 27/62*    (2006.01)
*H01J 27/02*    (2006.01)

(52) U.S. Cl.
CPC ........... *G01N 27/622* (2013.01); *H01J 27/022* (2013.01); *H01J 49/16* (2013.01); *H01J 49/168* (2013.01)

(58) Field of Classification Search
CPC ............ G01N 27/624; G01N 27/622; G01N 30/7206; G01N 30/461; G01N 30/88; B03C 3/017; B03C 3/41; B03C 3/49
USPC .... 250/281, 280, 287, 288, 286, 324, 423 R
See application file for complete search history.

(56) References Cited

U.S. PATENT DOCUMENTS 3,324,291 A * 6/1967 Hudson .............. G03G 15/0258
250/324
4,511,244 A * 4/1985 Baumeister ........ G03G 15/0258
219/216

(Continued)

FOREIGN PATENT DOCUMENTS

JP        S58135107 A    8/1983

OTHER PUBLICATIONS

International Search Report for PCT/GB2013/052469 dated Dec. 5, 2013.

*Primary Examiner* — David A Vanore
(74) *Attorney, Agent, or Firm* — Advent, LLP

(57) ABSTRACT

Systems and techniques for cleaning a corona discharge point are described. A controller (150) can be operatively coupled to a corona discharge point (108) to control the operation of the corona discharge point (1089. The controller (150) and the corona discharge point (108) can be included with, for example, an ion mobility spectrometry (IMS) system (100). The controller (150) can be used to operate the corona discharge point (108) at an operating voltage for a first time interval, with or without an additional higher pulse voltage, to produce a corona discharge, and to operate the corona discharge point (108) at a cleaning voltage greater than the operating voltage for a second time interval subsequent to the first time interval to produce a corona discharge. The effectiveness of the corona discharge point (108) can be monitored by, for instance, measuring a voltage necessary to produce a corona discharge at the corona discharge point (108), measuring a current produced at the corona discharge point (108) from a corona discharge, and so forth.

20 Claims, 3 Drawing Sheets

(56) References Cited

U.S. PATENT DOCUMENTS

| | | | | |
|---|---|---|---|---|
| 4,985,716 A * | 1/1991 | Hosaka | ............... | G01D 15/06 347/123 |
| 5,017,876 A * | 5/1991 | Wright | ............... | G01R 19/0061 324/459 |
| 7,150,780 B2 * | 12/2006 | Krichtafovitch | ............... | B03C 3/08 250/423 R |
| 7,456,390 B2 * | 11/2008 | Miller | ............... | G01N 27/624 250/281 |
| 7,456,394 B2 * | 11/2008 | Cameron | ............... | G01N 27/624 250/281 |
| 7,579,589 B2 * | 8/2009 | Miller | ............... | G01N 30/7206 250/281 |
| 7,608,818 B2 * | 10/2009 | Miller | ............... | G01N 27/624 250/281 |
| 8,048,200 B2 * | 11/2011 | Gefter | ............... | B03C 3/017 361/213 |
| 8,049,426 B2 * | 11/2011 | Krichtafovitch | ............... | C01B 13/11 250/423 R |
| 2001/0046394 A1 * | 11/2001 | Yamanaka | ............... | G03G 15/0291 399/170 |
| 2004/0164238 A1 * | 8/2004 | Xu | ............... | H01J 49/168 250/287 |
| 2005/0116166 A1 * | 6/2005 | Krichtafovitch | ............... | H01T 19/00 250/324 |
| 2007/0029477 A1 * | 2/2007 | Miller | ............... | G01N 27/624 250/290 |
| 2009/0189064 A1 * | 7/2009 | Miller | ............... | G01N 27/624 250/282 |

\* cited by examiner

CLEANING OF CORONA DISCHARGE ION SOURCE

BACKGROUND

Ion mobility spectrometry refers to an analytical technique that can be used to separate and identify ionized material, such as molecules and atoms. Ionized material can be identified in the gas phase based on mobility in a carrier buffer gas. Thus, an ion mobility spectrometer (IMS) can identify material from a sample of interest by ionizing the material and measuring the time it takes the resulting ions to reach a detector. An ion's time of flight is associated with its ion mobility, which relates to the mass and geometry of the material that was ionized. The output of an IMS detector can be visually represented as a spectrum of peak height versus drift time. In some instances, IMS detection is performed at an elevated temperature (e.g., above one hundred degrees Celsius (100° C.)). In other instances, IMS detection can be performed without heating. IMS detection can be used for military and security applications, e.g., to detect drugs, explosives, and so forth. IMS detection can also be used in laboratory analytical applications, and with complementary detection techniques such as mass spectrometry, liquid chromatography, and so forth.

SUMMARY

Systems and techniques for cleaning a corona discharge point are described. A controller can be operatively coupled to a corona discharge point to control the operation of the corona discharge point. The controller and the corona discharge point can be included with, for example, an IMS system. The controller can be used to operate the corona discharge point at an operating voltage for a first time interval, with or without an additional higher pulse voltage, to produce a corona discharge, and to operate the corona discharge point at a cleaning voltage greater than the operating voltage for a second time interval subsequent to the first time interval to produce a corona discharge. The effectiveness of the corona discharge point can be monitored by, for instance, measuring a voltage necessary to produce a corona discharge at the corona discharge point, measuring a current produced at the corona discharge point from a corona discharge, and so forth.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION

Corona discharge can be used to ionize material from a sample of interest for analysis with an IMS detector. For example, an IMS detector can include a conductor having a point where applying an electric potential difference to the conductor causes an electrical discharge via ionization of fluid around the conductor. This discharge occurs when the gradient of the electric field around the conductor is high enough to form a conductive region, but not sufficiently high to cause arcing. The point of this electrical discharge is typically referred to as a corona discharge point. As electrical potentials are applied to electrodes in the IMS detector, an electric field is generated that moves the ionized material from the corona discharge point. In some instances, the ionized material can be transported through a gate, and subsequently through a drift space to a collector electrode.

Over time, a corona discharge point can become coated with various substances that may reduce the effectiveness of the corona discharge. For instance, with an unheated explosive detector (e.g., an explosives detector that operates at the surrounding (ambient or room) temperature), a corona discharge point can become coated with compounds that condense onto the surface (e.g., when a sample probe is used to wipe a surface to obtain a sample, and the sample is then introduced to the IMS detector using a desorber to vaporize a portion of the sample). These substances may comprise, for instance, compounds having high boiling points. In some instances, a reaction region and/or an inlet of an IMS detector can be heated to reduce the deposition of dirt onto a corona discharge point. However, for a small portable device that is battery powered (e.g., a lightweight, handheld detector device), the power requirements for this type of constant heating can be prohibitive.

Figure 1A:
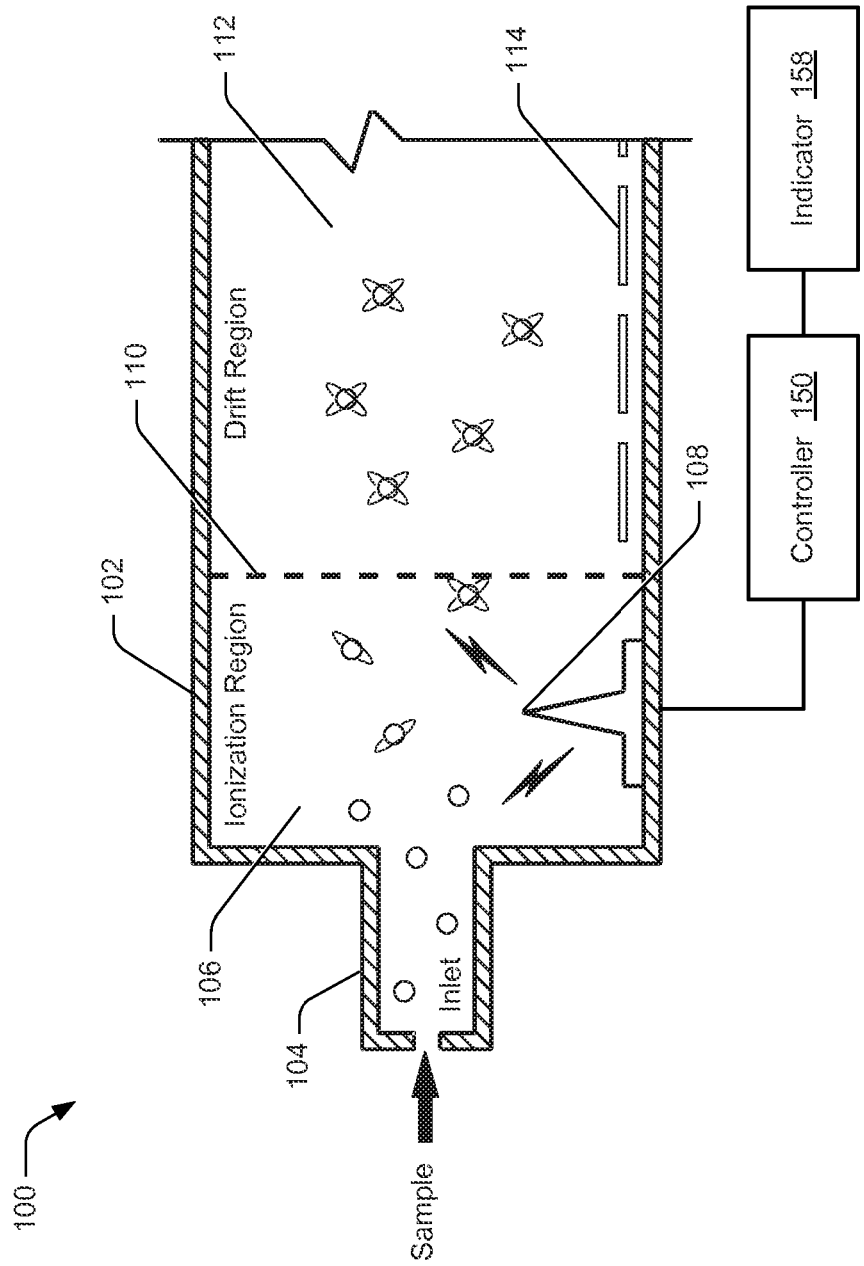
FIG. 1A is a diagrammatic illustration of a system including a controller operatively coupled with a corona discharge point of an IMS detector, where the controller can be used to control the operation of the corona discharge point to facilitate cleaning of the corona discharge point in accordance with example implementations of the present disclosure.

Techniques are described for cleaning a corona discharge point to maintain effectiveness that may otherwise be decreased by a coating on the corona discharge point. For example, as a corona discharge point becomes coated, increasingly higher voltages may be required to cause an electrical discharge. By periodically cleaning a corona discharge point, less voltage may be required to operate, for example, IMS detection equipment. Further, this technique can prevent corona discharge instability and/or failure of a corona discharge point. FIG. 1 is an illustration of a spectrometer system, such as an ion mobility spectrometer (IMS) system 100. Although IMS detection techniques are described herein, it should be noted that a variety of different spectrometers can benefit from the structures, techniques, and approaches of the present disclosure. It is the intention of this disclosure to encompass and include such changes.

IMS systems 100 can include spectrometry equipment that employs unheated (e.g., surrounding (ambient or room) temperature) detection techniques. For example, an IMS system 100 can be configured as a lightweight explosive detector. However, it should be noted that an explosive detector is provided by way of example only and is not meant to be restrictive of the present disclosure. Thus, techniques of the present disclosure may be used with other spectrometry configurations. For example, an IMS system 100 can be configured as a chemical detector. An IMS system 100 can include a detector device, such as an IMS detector 102 having a sample receiving port for introducing material from a sample of interest to an ionization region/chamber. For example, the IMS detector 102 can have an inlet 104 where air to be sampled is admitted to the IMS detector 102. In some implementations, the IMS detector 102 can have another device such as a gas chromatograph (not shown) connected in line with the IMS inlet 104.

The inlet 104 can employ a variety of sample introduction approaches. In some instances, a flow of air can be used. In other instances, IMS systems 100 can use a variety of fluids and/or gases to draw material into the inlet 104. Approaches for drawing material through the inlet 104 include the use of fans, pressurized gases, a vacuum created by a drift gas flowing through a drift region/chamber, and so forth. For example, the IMS detector 102 can be connected to a sampling line, where air from the surrounding environment (e.g., room air) is drawn into the sampling line using a fan. IMS systems 100 can operate at substantially ambient pressure, although a stream of air or other fluid can be used to introduce sample material into an ionization region. In other instances, IMS systems 100 can operate at lower pressures (i.e., pressures less than ambient pressure). Further, IMS systems 100 can include other components to furnish introduction of material from a sample source. For example, a desorber, such as a heater, can be included with an IMS system 100 to cause at least a portion of a sample to vaporize (e.g., enter its gas phase) so the sample portion can be drawn into the inlet 104. For instance, a sample probe, a swab, a wipe, or the like, can be used to obtain a sample of interest from a surface. The sample probe can then be used to deliver the sample to the inlet 104 of an IMS system 100. IMS systems 100 can also include a pre-concentrator to concentrate or cause a bolus of material to enter an ionization region.

A portion of a sample can be drawn through a small aperture inlet (e.g., a pinhole) into the IMS detector 102 using, for example, a diaphragm in fluid communication with an interior volume of the IMS detector 102. For instance, when the internal pressure in the interior volume is reduced by movement of the diaphragm, a portion of the sample is transferred from the inlet 104 into the IMS detector 102 through the pinhole. After passing through the pinhole, the sample portion enters an ionization region 106 where the sample is ionized using an ionization source, such as a corona discharge ionizer (e.g., having a corona discharge point 108). In some instances, the corona discharge point 108 can ionize material from a sample of interest in multiple steps. For example, the corona discharge point 108 can generate a corona that ionizes gases in the ionization region 106 that are subsequently used to ionize the material of interest. Example gases include, but are not necessarily limited to: nitrogen, water vapor, gases included in air, and so forth.

In implementations, the IMS detector 102 can operate in positive mode, negative mode, switch between positive and negative mode, and so forth. For example, in positive mode the corona discharge point 108 can generate positive ions from a sample of interest, while in negative mode the corona discharge point 108 can generate negative ions. Operation of the IMS detector 102 in positive mode, negative mode, or switching between positive and negative mode can depend on implementation preferences, a predicted sample type (e.g., explosive, narcotic, toxic industrial chemicals), and so forth. Further, the corona discharge point 108 can be pulsed periodically (e.g., based upon sample introduction, gate opening, the occurrence of an event, and so on).

The sample ions can then be directed toward a gating grid using an electric field. The gating grid can be opened momentarily to allow small clusters of sample ions to enter a drift region. For example, the IMS detector 102 can include an electronic shutter or gate 110 at the inlet end of a drift region 112. In implementations, the gate 110 controls entrance of ions to the drift region 112. For example, the gate 110 can include a mesh of wires to which an electrical potential difference is applied or removed. The drift region 112 has electrodes 114 (e.g., focusing rings) spaced along its length for applying an electric field to draw ions along the drift region 112 and/or to direct the ions toward a detector disposed generally opposite the gate 110 in the drift region 112. For example, the drift region 112, including the electrodes 114, can apply a substantially uniform field in the drift region 112. The sample ions can be collected at a collector electrode, which can be connected to analysis instrumentation for analyzing the flight times of the various sample ions. For instance, a collector plate at the far end of the drift region 112 can collect ions that pass along the drift region 112.

The drift region 112 can be used to separate ions admitted to the drift region 112 based on the individual ions' ion mobility. Ion mobility is determined by the charge on an ion, an ion's mass, geometry, and so forth. In this manner, IMS systems 100 can separate ions based on time of flight. The drift region 112 can have a substantially uniform electrical field that extends from the gate 110 to a collector. The collector can be a collector plate (e.g., a Faraday plate) that detects ions based on their charge as they contact the collector plate. In implementations, a drift gas can be supplied through the drift region 112 in a direction generally opposite the ions' path of travel to the collector plate. For example, the drift gas can flow from adjacent the collector plate toward the gate 110. Example drift gases include, but are not necessarily limited to: nitrogen, helium, air, air that is re-circulated (e.g., air that is cleaned and/or dried) and so forth. For example, a pump can be used to circulate air along the drift region 112 against the direction of flow of ions. The air can be dried and cleaned using, for instance, a molecular sieve pack.

In implementations, the IMS detector 102 can include a variety of components to promote identification of a material of interest. For example, the IMS detector 102 can include one or more cells containing a calibrant and/or a dopant component. Calibrant can be used to calibrate the measurement of ion mobility. Dopant can be used to prohibit the ionization of interferant ions. Dopant can also be combined with a sample material and ionized to form an ion that can be more effectively detected than an ion that corresponds to the sample material alone. Dopant can be provided to one or more of the inlet 104, the ionization region 106 and/or the drift region 112. The IMS detector 102 can be configured to provide dopant to different locations, possibly at different times during operation of the IMS detector 102. The IMS detector 102 can be configured to coordinate dopant delivery with operation of other components of an IMS system 100.

A controller 150 can detect the change in charge on the collector plate as ions reach it. Thus, the controller 150 can identify materials from their corresponding ions. In implementations, the controller 150 can also be used to control opening of the gate 110 to produce a spectrum of time of flight of the different ions along the drift region 112. For example, the controller 150 can be used to control voltages applied to the gate 110. Operation of the gate 110 can be controlled to occur periodically, upon the occurrence of an event, and so forth. For example, the controller 150 can adjust how long the gate 110 is open and/or closed based upon the occurrence of an event (e.g., corona discharge), periodically, and so forth. Further, the controller 150 can switch the electrical potential applied to the gate 110 based upon the mode of the ionization source (e.g., whether the IMS detector 102 is in positive or negative mode). In some instances, the controller 150 can be configured to detect the presence of explosives and/or chemical agents and provide a warning or indication of such agents on an indicator 158.

In implementations, an IMS system 100, including some or all of its components, can operate under computer control. For example, a processor can be included with or in an IMS system 100 to control the components and functions of IMS systems 100 described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the IMS systems 100. In the case of a software implementation, the module, functionality, or logic represents program code that performs specified tasks when executed on a processor (e.g., CPU or CPUs). The program code may be stored in one or more computer-readable memory devices (e.g., internal memory and/or one or more tangible media), and so on. The structures, functions, approaches, and techniques described herein can be implemented on a variety of commercial computing platforms having a variety of processors.

Figure 1B:
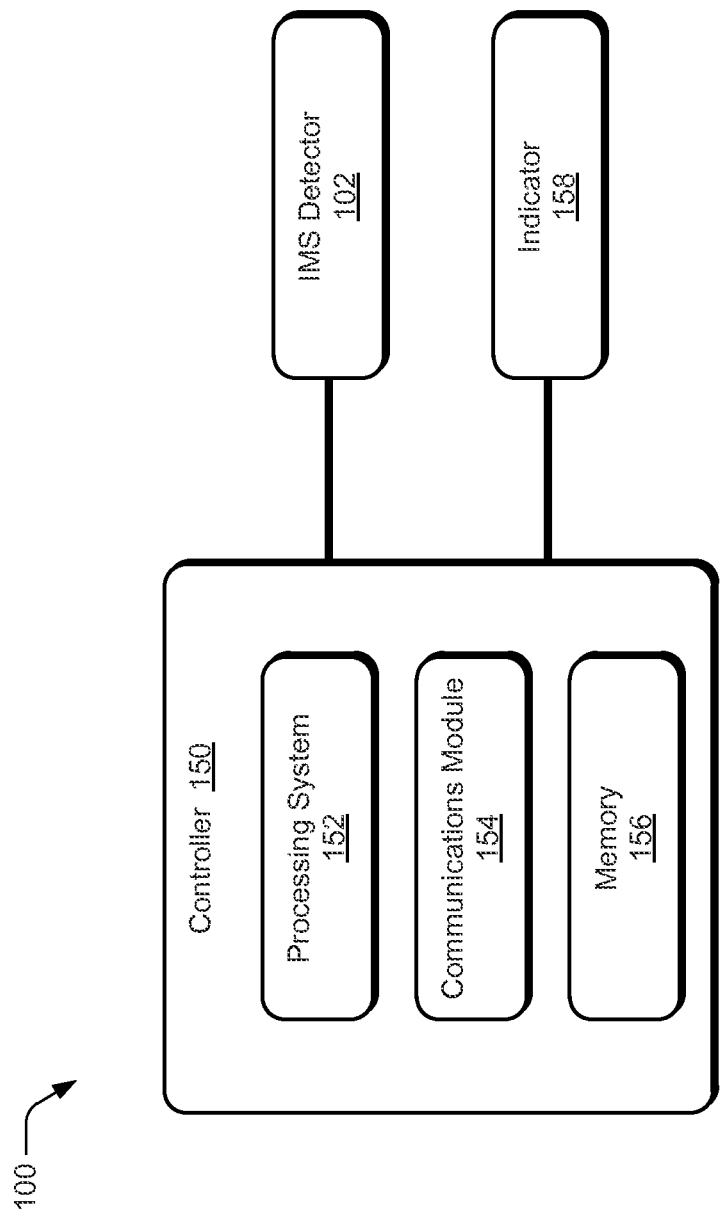
FIG. 1B is a diagrammatic illustration of a system including a controller operatively coupled with an IMS detector, where the controller can be used to control the operation of a corona discharge point to facilitate cleaning of the corona discharge point in accordance with example implementations of the present disclosure.

For example, as illustrated in FIG. 1B, the IMS detector 102 may be coupled with the controller 150 for controlling the IMS detector 102. The controller 150 may include a processing system 152, a communications module 154, and memory 156. The processing system 152 provides processing functionality for the controller 150, and may include any number of processors, micro-controllers, or other processing systems and resident or external memory for storing data and other information accessed or generated by the controller 150. The processing system 152 may execute one or more software programs, which implement techniques described herein. The processing system 152 is not limited by the materials from which it is formed or the processing mechanisms employed therein, and as such, may be implemented via semiconductor(s) and/or transistors (e.g., using electronic integrated circuit (IC) components), and so forth. The communications module 154 is operatively configured to communicate with components of the IMS detector 102. The communications module 154 is also communicatively coupled with the processing system 152 (e.g., for communicating inputs from the IMS detector 102 to the processing system 152). The communications module 154 and/or the processing system 152 can also be configured to communicate with a variety of different networks, including, but not necessarily limited to: the Internet, a cellular telephone network, a local area network (LAN), a wide area network (WAN), a wireless network, a public telephone network, an intranet, and so on.

The memory 156 is an example of tangible computer-readable media that provides storage functionality to store various data associated with operation of the controller 150, such as software programs and/or code segments, or other data to instruct the processing system 152 and possibly other components of the controller 150 to perform the steps described herein. Thus, the memory 156 can store data, such as a program of instructions for operating the IMS system 100 (including its components), spectral data, and so on. Although a single memory 156 is shown, a wide variety of types and combinations of memory (e.g., tangible, non-transitory memory) may be employed. The memory 156 may be integral with the processing system 152, may comprise stand-alone memory, or may be a combination of both.

The memory 156 may include, but is not necessarily limited to: removable and non-removable memory components, such as Random Access Memory (RAM), Read-Only Memory (ROM), Flash memory (e.g., a Secure Digital (SD) memory card, a mini-SD memory card, and/or a micro-SD memory card), magnetic memory, optical memory, Universal Serial Bus (USB) memory devices, hard disk memory, external memory, and other types of computer-readable storage media. In implementations, the IMS detector 102 and/or memory 156 may include removable Integrated Circuit Card (ICC) memory, such as memory provided by a Subscriber Identity Module (SIM) card, a Universal Subscriber Identity Module (USIM) card, a Universal Integrated Circuit Card (UICC), and so on.

In implementations, a variety of analytical devices can make use of the structures, techniques, approaches, and so on described herein. Thus, although IMS systems 100 are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Having described systems, components, techniques, modules, and approaches that can be implemented, in accordance with the present disclosure, sample procedures are now described that can be implemented with the systems, components, techniques, modules and approaches above.

Example Procedures

The following discussion describes procedures that may be implemented utilizing the previously described IMS system 100 components, techniques, approaches, and modules. Aspects of each of the procedures may be implemented in hardware, software, or a combination thereof. The procedures are shown as a set of blocks that specify operations performed by one or more devices (e.g., a spectrometer, a computer system controlling a spectrometer or spectrometer components) and are not necessarily limited to the order shown for performing the operations by the respective blocks. In portions of the following discussion, reference will be made to the IMS systems 100 of FIG. 1.

Figure 2:
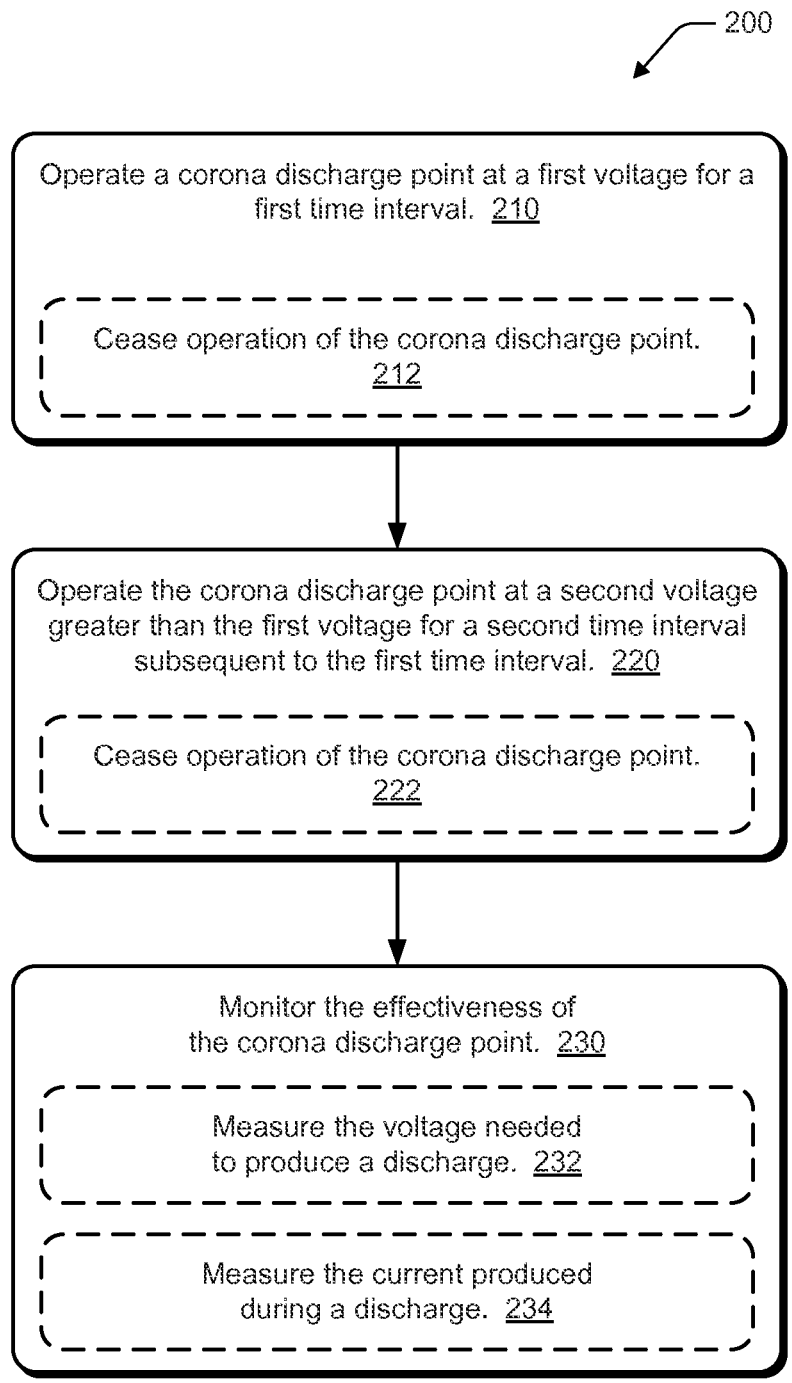
FIG. 2 is a flow diagram illustrating a method for controlling the operation of the corona discharge point to facilitate cleaning of the corona discharge point in accordance with example implementations of the present disclosure.

FIG. 2 depicts a procedure 200 in an example implementation in which a corona discharge point is periodically operated to clean the corona discharge point and maintain effectiveness that may otherwise be decreased by coating of the corona discharge point. For example, with reference to FIG. 1, corona discharge point 108 of IMS system 100 can be periodically used for a cleaning operation. This can provide an improved corona response to voltage after a cleaning period. In implementations, the procedure 200 is performed under computer control. For instance, with continuing reference to FIG. 1, controller 150 can be used to control operation of corona discharge point 108. In some instances, the procedure 200 can be used with a corona discharge point that produces a continuous discharge while operational. In other instances, the procedure 200 can be used with a corona discharge point that produces pulses on shorter time-scales, i.e., employing discontinuous operation of a corona discharge point. For example, with a pulsed implementation, where there are periods of inactivity between pulses, a corona discharge point may be more susceptible to a coating effect.

A corona discharge point can be operated at a first (operating) voltage (e.g., a direct current (DC) voltage) for a first time interval (Block 210). For example, the corona discharge point can be operated continuously at a voltage of about eight hundred volts (800 V) for a first time interval. It should be noted that this voltage is provided by way of example only and is not meant to be restrictive of the present disclosure. Thus, the corona discharge point can be operated at one or more other voltages during the first time interval. In some instances, operation of the corona discharge point may cease immediately following the first time interval (Block 212), such as when the corona discharge point is operated non-continuously, e.g., in a pulsed implementation. In other non-continuous instances, an additional higher voltage may be applied for a short time period and then removed. For instance, the corona discharge point can be operated at a continuous voltage of about eight hundred volts (800 V) with a higher voltage of about one and one-half kilovolts (1.5 kV) applied during a pulse portion of the first time interval. In this implementation, the voltage of about eight hundred volts (800 V) is referred to as the first (operating) voltage of the corona discharge point. It should be noted that for the purposes of the present disclosure, the term "continuous" with reference to corona discharge point operation can encompass operation while voltage is applied continuously. However, the resulting corona discharge may be either continuous or intermittent. For example, the corona discharge may be sporadic at times when continuous voltage is insufficient to produce a corona discharge, such as when a corona discharge point becomes increasingly coated with material.

Then, the corona discharge point can be operated at a second (cleaning) voltage greater than the first voltage for a second time interval subsequent to the first time interval (Block 220). For example, the corona discharge point can be operated at a voltage of about two thousand volts (2 kV) for a second time interval. It should be noted that this voltage is provided by way of example only and is not meant to be restrictive of the present disclosure. Thus, the corona discharge point can be operated at one or more other voltages during the second time interval. Further, it should be noted that the second voltage may be greater than the first (operating) voltage of the corona discharge point but less than, equal to, or greater than another voltage of the corona discharge point used during the first time interval. For example, in the previous example, where the corona discharge point is operated at a continuous voltage of about eight hundred volts (800 V) with a pulse voltage of about one and one-half kilovolts (1.5 kV), the second voltage can be less than the pulse voltage of one and one-half kilovolts (1.5 kV), equal to 1.5 kV, or greater than 1.5 kV. In implementations, the corona discharge point can be operated for a second time period lasting between at least approximately two seconds (2 sec) and approximately ten minutes (10 min). For example, in a particular instance, the corona discharge point can be operated continuously for approximately ten seconds (10 sec). Continuous operation of the corona discharge point at the second voltage can create a corrosive environment that can remove residue from the corona discharge point. In some instances, operation of the corona discharge point may cease immediately following the second (cleaning) time interval (Block 222), such as when the corona discharge point is operated non-continuously, e.g., in a pulsed implementation. However, in other implementations, the corona discharge point may continue to operate as previously described.

After the cleaning period during the second time interval, the voltage may be reduced, and operation of the corona discharge point can return to, for instance, its normal pulsed or continuous mode. Then, during subsequent operation, the effectiveness of the corona discharge point may be improved. For example, the corona discharge point can be operated at the operating voltage for a third time interval subsequent to the second time interval. For example, the corona discharge point can be operated at a voltage of about eight hundred volts (800 V) for a third time interval, with or without an additional higher voltage for pulsed operation. It should be noted that this voltage is provided by way of example only and is not meant to be restrictive of the present disclosure. Thus, the corona discharge point can be operated at one or more other voltages during the third time interval. As previously discussed, operation of the corona discharge point may cease immediately following the third time interval, such as when the corona discharge point is operated non-continuously, e.g., in a pulsed implementation. In other implementations, the corona discharge point may continue to operate. For instance, the corona discharge point can be operated at a continuous voltage of about eight hundred volts (800 V) with a higher voltage of about one and one-half kilovolts (1.5 kV) applied during a pulse portion of the first time interval as previously described.

In some instances, the health of a corona discharge point can be monitored, and cleaning periods can be applied to respond to reduced corona discharge point effectiveness. For example, the effectiveness of a corona discharge point can be monitored (Block 230). In a pulsed configuration, the effectiveness can be monitored so that when the corona discharge point is determined to be sufficiently dirty, continuous corona discharge can be induced to remove substances that have condensed on the discharge point. Thus, feedback can be collected regarding the effectiveness of the corona discharge during a detection operation and/or during a cleaning operation. This feedback can be used to control one or more characteristics of a cleaning operation, such as, but not necessarily limited to: frequency of cleaning, duration of cleaning, applied voltage, induced current, and so forth. One or more components of a detection system can be used to monitor the health of a corona discharge point, and a feedback loop can be used to adjust the cleaning operation of the system. Accordingly, the operation described at Block 220 may be performed repeatedly and/or between regular operations of an IMS system depending upon measured performance, design preferences, and so forth.

The effectiveness of a corona discharge point may be monitored by measuring the voltage necessary to produce a corona discharge at a corona discharge point (Block 232). For example, as a corona discharge point gets dirty, the voltage necessary to produce a discharge may increase. The voltage needed to produce a discharge can be measured during a detection operation and/or during a cleaning operation. For example, the necessary voltage can be measured during a cleaning operation to monitor how well the cleaning process is progressing. The necessary voltage can also be measured between cleaning periods, such as during a detection operation. In implementations, a corona discharge point can be operated, the operation may be stopped while the required voltage is measured, and then the cleaning operation can be started again. This process can be repeated until a sufficient operational efficiency is achieved. In other instances, the corona discharge point can continue to operate while one or more cleaning measurements are obtained.

The voltage necessary to produce a corona discharge can also be measured to determine an appropriate voltage for a cleaning operation. For instance, the required voltage for producing a discharge can be measured, and the voltage for operating the discharge point during cleaning can be set at or above the measured voltage. It should be noted that one or more operational characteristics other than, or in addition to, voltage can be used to determine the effectiveness of a corona discharge point and/or a required operational characteristic for operating a corona discharge point in a cleaning mode. For example, the effectiveness of a corona discharge point may be monitored by measuring the current produced from a corona discharge at a corona discharge point (Block 234). In some instances, operational characteristics of a current electrode and/or characteristics associated with operation of a preamplifier for a current electrode of an IMS detection system can be monitored to gauge the effectiveness of a cleaning operation. One or more of these characteristics can also be used to set operational characteristics of a corona discharge point during a cleaning operation. In other instances, separate detection equipment may be included in the reaction region of an IMS detection system (e.g., to measure ion current from a corona discharge).

Further, components of an IMS detection system can be operated in various modes to facilitate the determination of operational effectiveness and/or cleaning effectiveness. For example, in some instances, a gating grid can be left in an open configuration longer during a cleaning operation than it would otherwise be opened during a detection operation to gather more time dependent information regarding cleaning effectiveness. In other implementations, a gating grid may be left in a closed orientation to obtain more accurate measurements for a corona discharge. Regular cleaning periods can be scheduled as part of internal device health checks and/or device maintenance. Cleaning operations can also be executed as part of the normal operation of an IMS detection system. For instance, one or more cleaning cycles can be initiated each time a device is activated, deactivated, and so forth. In some instances, a cleaning operation can be initiated during a battery charging cycle. Additionally, cleaning can be initiated based upon operational parameters for an IMS detection system. For example, the duration of cleaning operations can be increased incrementally (e.g., lengthening in duration as a device is continually operated).

A controller can be operatively coupled to a corona discharge point to control the operation of the corona discharge point. The controller and the corona discharge point can be included with, for example, an IMS system. The controller can be used to operate the corona discharge point at an operating voltage for a first time interval, with or without an additional higher pulse voltage, to produce a corona discharge, and to operate the corona discharge point at a cleaning voltage greater than the operating voltage for a second time interval subsequent to the first time interval to produce a corona discharge. The effectiveness of the corona discharge point can be monitored by, for instance, measuring a voltage necessary to produce a corona discharge at the corona discharge point, measuring a current produced at the corona discharge point from a corona discharge, and so forth.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:

1. A system comprising:
   an ion mobility spectrometer (IMS) detector comprising a corona discharge point for producing a corona discharge; and
   a processing system operatively coupled with the IMS detector for operating the corona discharge point, the processing system configured to operate the corona discharge point at an operating voltage for a first time interval to produce a corona discharge, and to operate the corona discharge point at a cleaning voltage greater than the operating voltage for a second time interval subsequent to the first time interval to produce a corona discharge.

2. The system as recited in claim 1, wherein the processing system is configured to cause the corona discharge point to cease operation immediately following the first time interval.

3. The system as recited in claim 1, wherein the processing system is configured to cause the corona discharge point to cease operation immediately following the second time interval.

4. The system as recited in claim 1, wherein the processing system is configured to operate the corona discharge point at a second operating voltage less than the cleaning voltage for a third time interval subsequent to the second time interval to produce a corona discharge.

5. The system as recited in claim 1, wherein the processing system is configured to determine an effectiveness of the corona discharge point by receiving a voltage necessary to produce a corona discharge at the corona discharge point.

6. The system as recited in claim 1, wherein the processing system is configured to determine an effectiveness of the corona discharge point by receiving a current produced at the corona discharge point from a corona discharge.

7. A method comprising: operating a corona discharge point at an operating voltage for a first time interval to produce a corona discharge;
operating the corona discharge point at a cleaning voltage greater than the operating voltage for a second time interval subsequent to the first time interval to produce a corona discharge.

8. The method as recited in claim 7, further comprising ceasing operation of the corona discharge point immediately following the first time interval.

9. The method as recited in claim 7, further comprising ceasing operation of the corona discharge point immediately following the second time interval.

10. The method as recited in claim 7, further comprising operating the corona discharge point at a second operating voltage less than the cleaning voltage for a third time interval subsequent to the second time interval to produce a corona discharge.

11. The method as recited in claim 7, further comprising monitoring an effectiveness of the corona discharge point and adjusting the cleaning voltage based upon the monitored effectiveness of the corona discharge point.

12. The method as recited in claim 11, wherein monitoring an effectiveness of the corona discharge point comprises measuring a voltage necessary to produce a corona discharge at the corona discharge point.

13. The method as recited in claim 11, wherein monitoring an effectiveness of the corona discharge point comprises measuring a current produced at the corona discharge point from a corona discharge.

14. An apparatus comprising:
a corona discharge point for producing a corona discharge; and
a controller operatively coupled with the corona discharge point for controlling the corona discharge, the controller configured to operate the corona discharge point at an operating voltage for a first time interval to produce a corona discharge, and to operate the corona discharge point at a cleaning voltage greater than the operating voltage for a second time interval subsequent to the first time interval to produce a corona discharge.

15. The apparatus as recited in claim 14, wherein the controller is configured to cease operation of the corona discharge point immediately following the first time interval.

16. The apparatus as recited in claim 14, wherein the controller is configured to cease operation of the corona discharge point immediately following the second time interval.

17. The apparatus as recited in claim 14, wherein the controller is configured to operate the corona discharge point at a second operating voltage less than the cleaning voltage for a third time interval subsequent to the second time interval to produce a corona discharge.

18. The apparatus as recited in claim 14, wherein the controller is configured to monitor an effectiveness of the corona discharge point.

19. The apparatus as recited in claim 18, wherein the controller is configured to monitor the effectiveness of the corona discharge point by measuring a voltage necessary to produce a corona discharge at the corona discharge point.

20. The apparatus as recited in claim 18, wherein the controller is configured to monitor the effectiveness of the corona discharge point by measuring a current produced at the corona discharge point from a corona discharge.

* * * * *